(12) United States Patent
Yu

(10) Patent No.: US 8,500,748 B2
(45) Date of Patent: Aug. 6, 2013

(54) TOOL AND COMPONENT ENGAGING MECHANISM

(75) Inventor: Kidong Yu, Memphis, TN (US)

(73) Assignee: Wasaw Orthopedic, Inc., Warsaw, IN (US)

( * ) Notice: Subject to any disclaimer, the term of this patent is extended or adjusted under 35 U.S.C. 154(b) by 475 days.

(21) Appl. No.: 12/567,173

(22) Filed: Sep. 25, 2009

(65) Prior Publication Data

US 2011/0077693 A1    Mar. 31, 2011

(51) Int. Cl.
    *A61B 17/60*    (2006.01)
    *A61F 2/00*    (2006.01)

(52) U.S. Cl.
    USPC ......................................................... 606/99

(58) Field of Classification Search
    USPC .................... 606/99, 104; 411/408; 81/436, 81/451, 460, 461
    See application file for complete search history.

(56) References Cited

U.S. PATENT DOCUMENTS

| | | | |
|---|---|---|---|
| 2,627,778 A | 2/1953 | Hodell | |
| 3,885,492 A | 5/1975 | Gutshall | |
| 4,105,056 A * | 8/1978 | Arnn | 81/436 |
| 4,452,556 A | 6/1984 | Nelson et al. | |
| 4,457,654 A | 7/1984 | Sygnator | |
| 4,936,172 A | 6/1990 | Jackson | |
| 5,438,895 A | 8/1995 | Bassell et al. | |
| 5,582,548 A | 12/1996 | Czegledi | |
| 5,645,546 A | 7/1997 | Fard | |
| 5,722,833 A | 3/1998 | Fischer et al. | |
| 5,722,838 A * | 3/1998 | Czegledi | 411/407 |
| 6,016,727 A | 1/2000 | Morgan | |
| 6,149,653 A * | 11/2000 | Deslauriers | 606/232 |
| 6,209,426 B1 * | 4/2001 | Takahashi | 81/451 |
| RE37,153 E * | 5/2001 | Henszey et al. | 138/26 |
| 6,302,630 B1 * | 10/2001 | Grant | 411/372.6 |
| 6,526,851 B1 | 3/2003 | Fuerle | |
| 6,620,167 B2 | 9/2003 | Deslauriers et al. | |
| 6,626,067 B1 | 9/2003 | Iwinski et al. | |
| 6,681,662 B2 * | 1/2004 | Blackston | 81/451 |
| 7,128,513 B2 | 10/2006 | Walker | |
| 7,914,539 B2 * | 3/2011 | Stone et al. | 606/104 |
| 2003/0000351 A1 * | 1/2003 | Hawkes | 81/451 |
| 2006/0254397 A1 | 11/2006 | Mark et al. | |
| 2008/0288000 A1 * | 11/2008 | Cawley | 606/291 |
| 2009/0074536 A1 | 3/2009 | Dilling | |

* cited by examiner

*Primary Examiner* — Anu Ramana

(57) ABSTRACT

A component with an engaging mechanism is disclosed. The component comprises a proximal end and a distal end, wherein the proximal end is configured to cooperate with a tool. The proximal end comprises an outer portion configured for cooperating with the tool and an inner portion configured for cooperating with the tool, wherein the inner portion comprises an engaging element configured for cooperating with a distal portion of the tool so that the engaging element provides a temporary engagement between the component and the distal portion of the tool. A system for engaging a component with a tool also is disclosed.

20 Claims, 4 Drawing Sheets

TOOL AND COMPONENT ENGAGING MECHANISM

FIELD OF INVENTION

The present disclosure is directed to systems for temporarily engaging tools with fasteners or other components.

BACKGROUND

The present disclosure relates to systems for temporarily engaging tools with fasteners or other components. One embodiment relates to temporarily engaging a screwdriver with a screw.

SUMMARY OF THE INVENTION

A component with engaging mechanism is disclosed. The component comprises a proximal end and a distal end, wherein the proximal end is configured to cooperate with a tool. The proximal end comprises an outer portion configured for cooperating with the tool and an inner portion configured for cooperating with the tool, wherein the inner portion comprises an engaging element configured for cooperating with a distal portion of the tool so that the engaging element provides a temporary engagement between the component and the distal portion of the tool.

Additional aspects and features of the present disclosure will be apparent from the detailed description and claims as set forth below.

DETAILED DESCRIPTION

Figure 1:
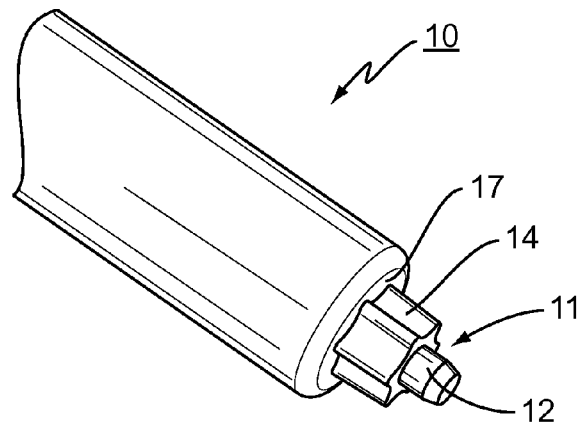
FIG. 1 is an isometric view of a distal end of a tool.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows an isometric view of a distal end 11 of a tool 10. In FIG. 1, the tool 10 is a screwdriver, but the tool may be another tool with a primary function different than that of a screwdriver. The primary function of a screwdriver is to drive screws into or out of a material, which may be accomplished by turning such screws. Although not shown in FIG. 1, the proximal end of a tool 10 is located opposite that of the distal end 11 of the tool 10. The proximal end of a tool 10, such as a screwdriver, comprises a handle for manipulation of the tool 10 by a user. As shown in FIG. 1, the tool 10 comprises a tool with an operative portion 14 and a non-operative portion 12, wherein the operative portion of the tool provides a primary function of the tool, and the non-operative portion of the tool 10 provides a function of temporary engagement between a component and a distal portion 11 of the tool 10. In the case where the tool 10 is a screwdriver, the component is a fastener such as screw and the primary function of the screwdriver is different than the function of temporary engagement. Also shown in FIG. 1, the non-operative portion 12 of the tool 10 is situated on the tool 10 at a location that is more distal than the operative portion 14. Further, FIG. 1 shows a bottom surface 17 of the distal portion 11 of tool 10.

Figure 2:
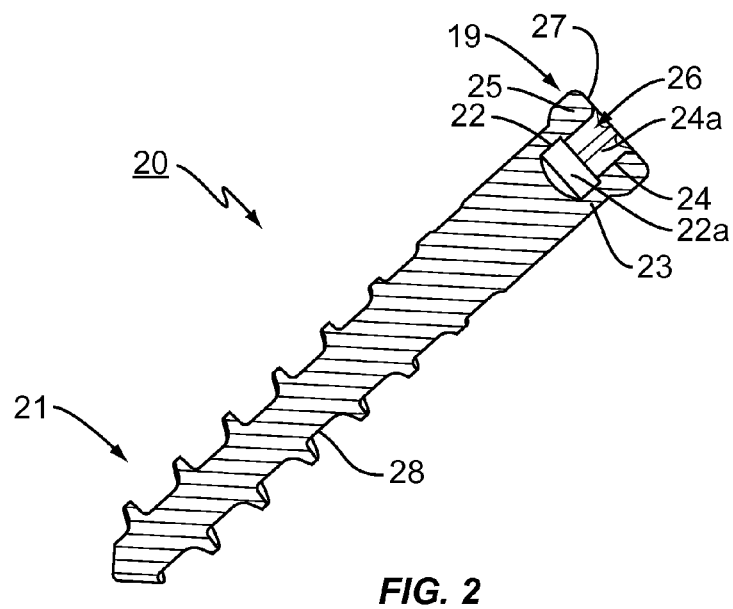
FIG. 2 is a cross-sectional view of a component.

FIG. 2 shows a cross-sectional view of a component 20. In FIG. 2, the component 20 is a fastener, and more specifically, a screw. As shown in FIG. 2, the component 20 comprises a proximal end 19 and a distal end 21, wherein the proximal end 19 is configured to cooperate with a tool 10. Further, as shown in FIG. 2, the proximal end 19 comprises an outer portion 25 configured for cooperating with the tool and an inner portion 23 configured for cooperating with the tool 10, wherein the inner portion 23 comprises an engaging element (not shown in FIG. 2, but shown in FIG. 3 by reference numeral 30) configured for cooperating with the distal portion 11 of the tool 10 so that the engaging element 30 provides a temporary engagement between the component 20 and the distal portion 11 of the tool 10.

Also shown in FIG. 2, the outer portion 25 of the component 20 has an inner surface 24 that defines an interior space 24a in the outer portion 25 of the component 20 that is configured to engage the operative portion 14 of the tool. Also shown in FIG. 2, the inner portion 23 has an inner surface 22 that defines an interior space 22a in the inner portion 23 of the component 20 that is configured to cooperate with the non-operative portion 12 of the tool 10. The combination of the interior space 24a of the outer portion 25 of the component 20 and the interior space 22a of the inner portion of the component 20 make up a total interior space 26. Further, as the component 20 of FIG. 2 is a screw, the distal end 21 of the component 20 has a threaded portion 28.

Figure 3:
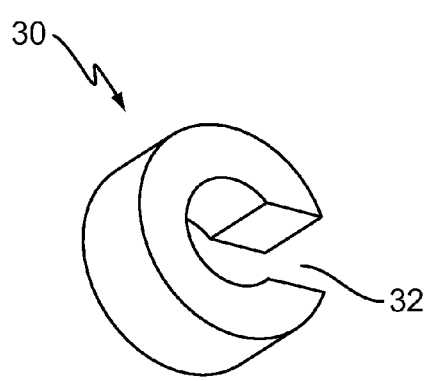
FIG. 3 is an isometric view of an engaging element.

FIG. 3 shows an isometric view of an engaging element 30, which provides a temporary engagement between the component 20 and the non-operative portion 12 of the tool 10. As shown in FIG. 3, the engaging element 30 has the shape that is a portion of an annular ring. As shown in FIG. 3, the engaging element 30 does not have the shape of an annular ring because of a gap designated by reference numeral 32. In certain embodiments, however, the engaging element 30 may have the shape of an annular ring. Described another way, the engaging element 30 substantially has the shape of a "C." The term "substantially" as used herein may be applied to modify any quantitative representation which could permissibly vary without resulting in a change in the basic function to which it is related. For example, the engaging element 30 may be considered substantially "C"-shaped if it has a gap 32 and helps provide the function of temporarily engaging the tool 10 with the fastener 20.

Figure 4:
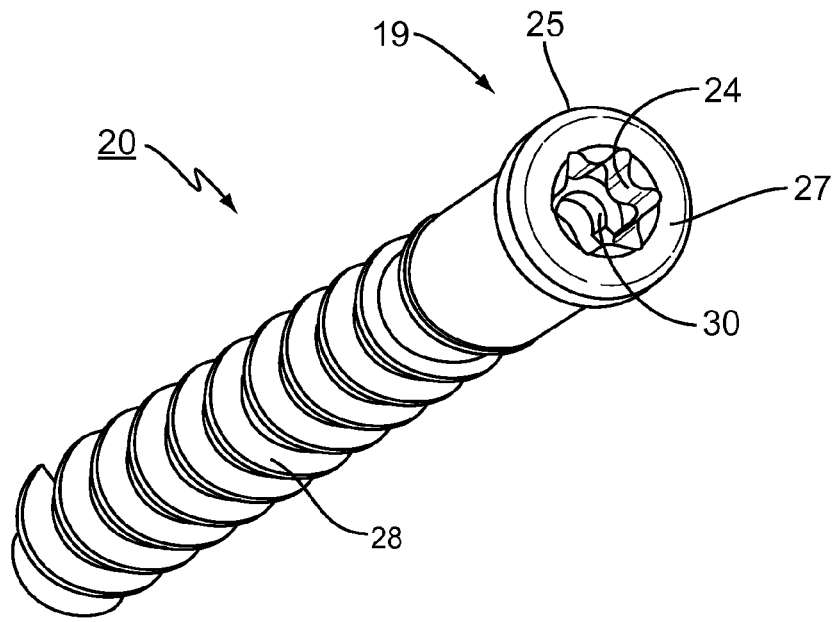
FIG. 4 is an isometric view of a portion of the component of FIG. 2 in conjunction with an engaging element.

FIG. 4 shows an isometric view of a portion of the component 20 of FIG. 2 in conjunction with an engagement element 30. In particular, FIG. 4 shows the engaging element 30 in place in the proximal end 19 of the component 20. Also, FIG.

4 shows the inner surface 24 of outer portion 25, as well as a top surface 27 of the component 20.

Figure 5:
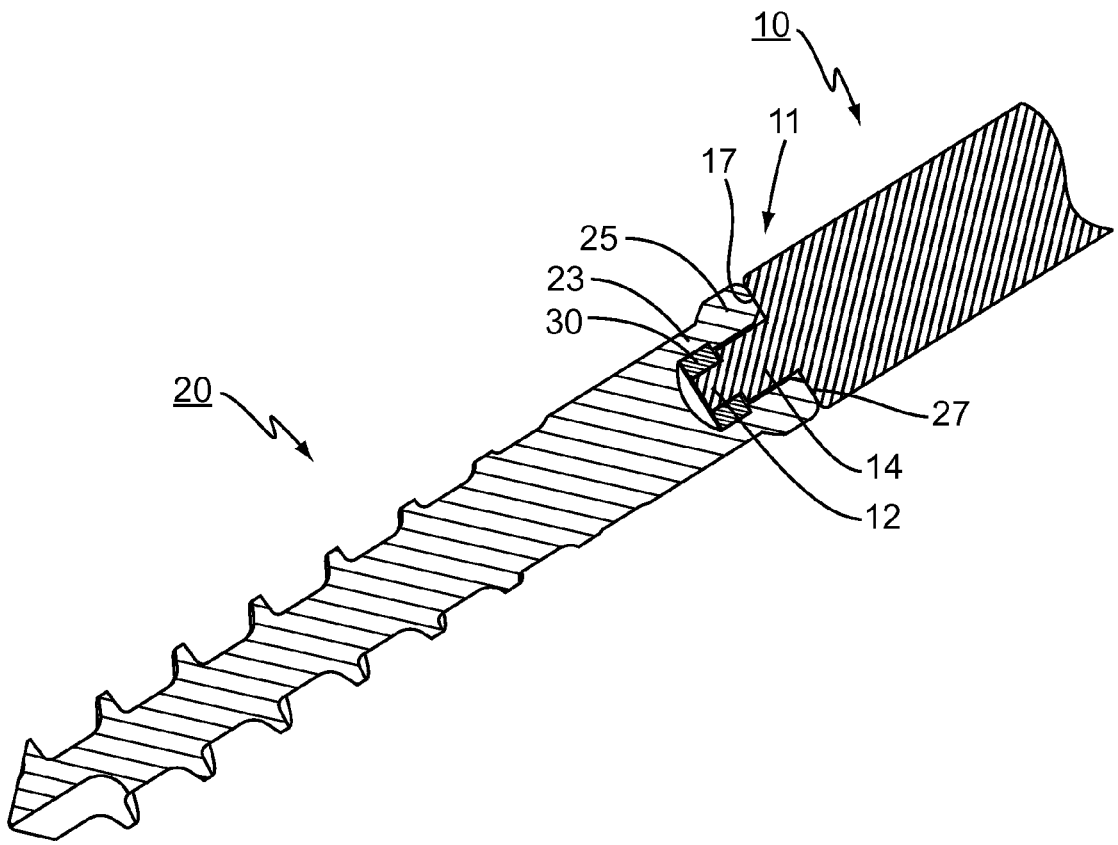
FIG. 5 is a cross-sectional view of a distal portion of the tool of FIG. 1 in conjunction with a proximal portion of the component of FIG. 4.

FIG. 5 shows a cross-sectional view of the distal portion 11 of the tool 10 of FIG. 1 in conjunction with the proximal portion 19 of the component 20 of FIG. 4. In this way, FIG. 5 shows a system for engaging the component 20 and the tool 10. In particular, FIG. 5 shows the bottom surface 17 of the distal portion 11 of tool 10 in contact with the top surface 27 of the component 20. As shown, the outer portion 25 of the component 20 is engaged with an operative portion 14 of the tool 10, and the inner portion 23 of the component 20 is engaged with the non-operative portion 12 of the tool 10. Further, the inner portion 23 has an inner surface 22 that defines a first interior space 22a in the inner portion 23 of the component 20, and the engaging element 30 is situated in the interior space 22a of the inner portion 23 such that the engaging element 30 defines a second interior space of the inner portion 23. Such second interior space of the inner portion 23 is smaller than the first interior space 22a of the inner portion 23 and configured for receiving the non-operative portion 12 of the tool 10. Further, the first interior space 24a of the inner portion 23 is larger than the interior space 22a of the outer portion 25, and the second interior space of the inner portion 23 is smaller than the interior space 24a of the outer portion 25.

The engaging element 30 may be fused to the component 20, or may not be fused to the component 20. In certain embodiments where the engaging element 30 is substantially "C"-shaped, the engaging member 30 may be slid into place in the first interior portion 22a of the inner portion 23 of the component 20. The engaging element 30 may be compressed to facilitate placement in its intended location (as shown in FIGS. 4 and 5), and the engaging element 30 reverts back to a more uncompressed state when it reaches its intended location. Once in place in its intended position of FIGS. 4 and 5, a component 20 may be placed on the distal portion 11 of the tool 10. When the top surface 27 of the component 20 contacts the bottom surface 17 of the distal portion 11 of the tool 10, the engaging element 30 imparts a certain amount of pressure against the non-operative portion 12 of the tool 10. Such pressure imparted by the engaging element 30 strengthens the grip that the tool 10 has on the component 20. This mechanism results in a temporary engagement between the component 20 and the distal portion 12 of the tool 10. Such engagement is considered temporary because subsequent separation of the component 20 from the tool 10 is not significantly more difficult than if an engaging element 30 was not utilized. Note that the engaging element 30 need not be substantially "C" shaped. That is, the engaging element 30 may have the shape of a portion or portions of an annular ring, but not be C-shaped. Specifically, and for example, the engaging element 30 may be arc-shaped, or may comprise one or more segments, either arc-shaped or not, so long as the temporary engagement function is accomplished. The engaging element 30 may be a biocompatible material such as, for example, polyetheretherketone ("PEEK"), polyethylene, stainless steel, titanium, cobalt chrome, polyurethane, silicone or Nickel Titanium ("Nitinol" or "NiTi").

As noted, the engaging element 30 may be fused to component 20. An example of such embodiment or embodiments is that the engaging element 30 may be molded into the component 20. The shapes of such fused or molded embodiments may be, for example, any of the shapes of the above-described non-fused embodiments. Suitable materials for fused embodiments may include, for example, polyurethane, silicone or other material capable of being fused or molded to the component. Materials also may be biocompatible.

Figure 6:
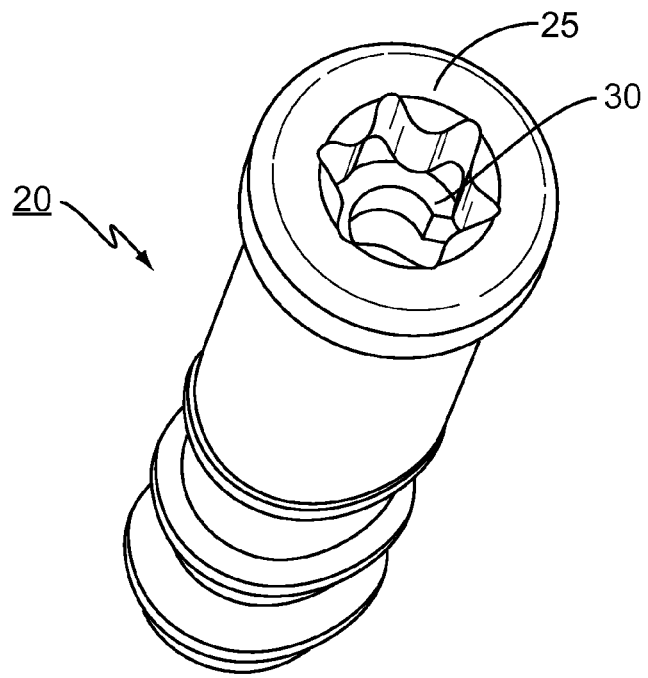
FIG. 6 is a an isometric view of a hexalobular head design for a component.
Figure 7:
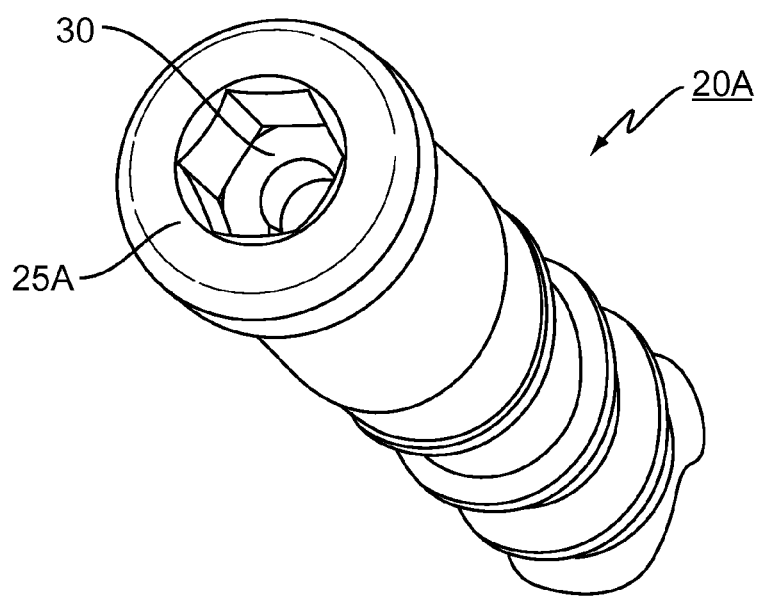
FIG. 7 is an isometric view of a hexagonal socket head design for a component.

Although many tools 10 and many components 20 are contemplated by the present disclosure and covered by the claims, the present disclosure focuses on embodiments where the component 20 is a screw (or other fastener), the tool 10 is a screwdriver, and the proximal end of the screw is a screw head. Further, the head of the component 20 of this disclosure may vary. FIG. 6 shows an isometric view of a hexalobular head design (or Torx) for a screw 20 (a view similar to that of FIG. 4), while FIG. 7 shows a hexagonal socket head design (or Allen) for a screw 20A. Other embodiments of the present disclosure are applicable to additional screw head designs, such as, for example, slotted, Phillips, Pozidriv, Robertson, Tri-Wing, Torq-set, triple-square, Polydrive, one-way—Clutch, Spline drive, Double hex and Bristol. Similarly, additional embodiments of the disclosure are contemplated wherein the tool surrounds the outer surface of a component such as where the tool uses an external driver (as opposed those disclosed in the figures where the tool is designed to engage an internal portion of the component), for example, for use with fasteners having Hex or Square head designs, or hexalobular. In such embodiments, an engaging element may be situated on the outside surface and a certain distance below the top of the component (or in the case of a fastener, below head of the fastener) and molded to the component. In such embodiments, the part of the component on and around the engaging element, as well as the non-operative portion of the tool will each be configured to cooperate with each other to provide a function of temporary engagement.

Figure 8:
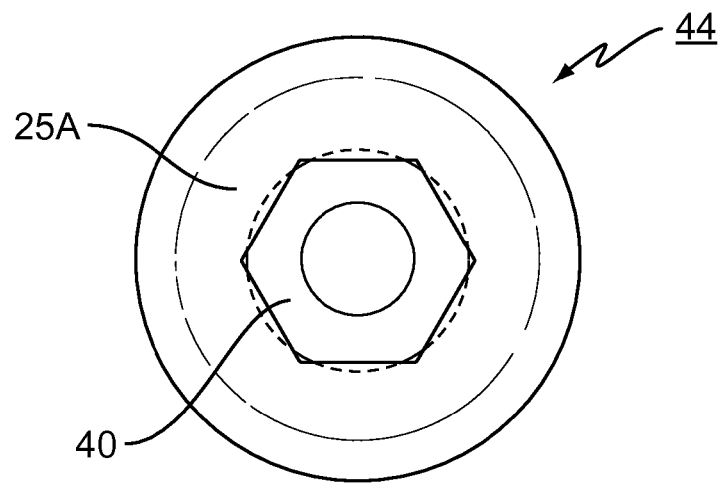
FIG. 8 is a top view of a component having a hexagonal socket head design with an engaging element that has the shape of an annular ring.
Figure 9:
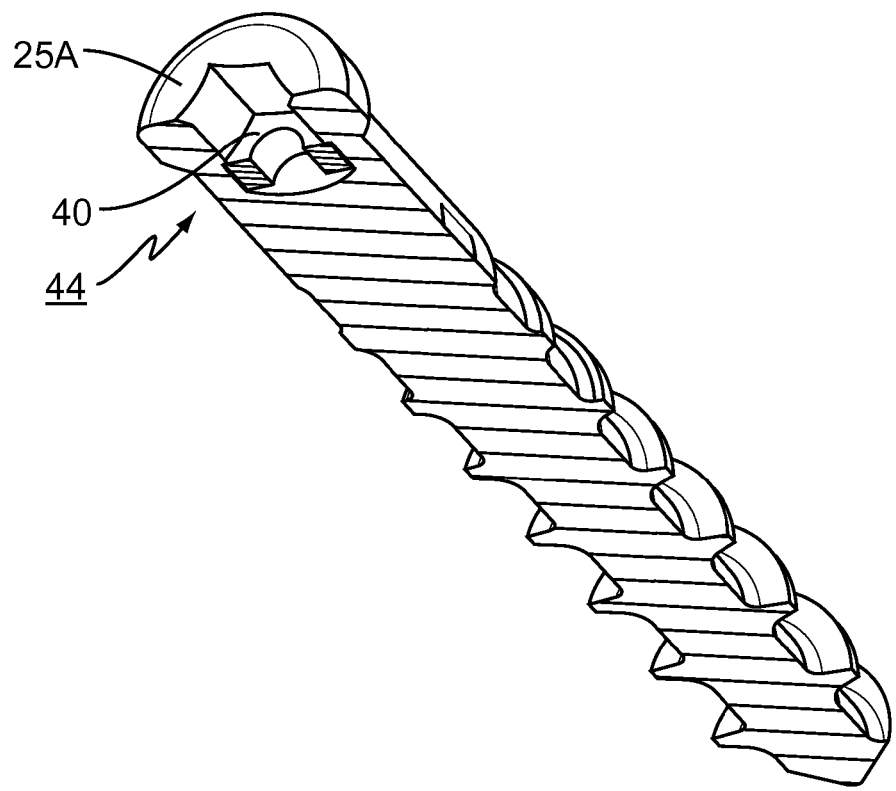
FIG. 9 is a cross-sectional view of the component of FIG. 8.

FIG. 8 shows a top view of a hexagonal socket head design 25A of component 44 with an engaging element 40 that has the shape of an annular ring. That is, the engaging element 40 of component 44 is a complete ring of circular shape. FIG. 9 shows a cross-sectional view of component 44. Note that with any embodiments according to the present disclosure, the engaging element 30 or 40 need not be circular in general shape. For example, an engaging element 30 or 40 may be more square shaped than that shown in the figures, and/or the corresponding non-operative portion of a tool, and the corresponding interior space of the inner portion of the component may have more square-shaped cross sections to accommodate and work with a more square-shaped engaging element 30 or 40. Further, the engaging element 40 of FIGS. 8 and 9 may be molded or fused to the component 44.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. For example, an embodiment of the disclosure may be a screwdriver for temporary engagement with a screw for use in medical applications, and more specifically, for example, may be used as a screwdriver designed for temporary engagement with a bone screw, i.e., a screw for fastening something to bone, such as, for example, fastening a portion of a plate or a portion of an artificial disc or a portion of a spacer to a vertebral body or vertebral bodies of a human spine. Furthermore, as used herein, the terms components and modules may be interchanged. It is understood that all spatial references, such as "superior," "inferior," "anterior," "posterior," "outer," "inner," and "perimeter" are for illustrative purposes only and can be varied within the scope of the disclosure.

The invention claimed is:

1. A component with engaging mechanism, the component comprising:

a proximal end and a distal end, wherein the proximal end is configured to cooperate with a tool having a non-operative portion and an operative portion and the proximal end comprises an inner surface defining:
- an outer portion configured for cooperating with the operative portion of the tool;
- an inner portion configured for cooperating with the non-operative portion of the tool;
- a ledge positioned at an interface between the inner and outer portions; and
an engaging element removably disposed in the inner portion such that an upper surface of the engaging element engages a lower surface of the ledge to retain the engaging element in the inner portion, wherein the engaging element is a C-shaped ring configured to apply pressure against the non-operative portion for strengthening a grip that the tool has on the component and provides for a temporary engagement.

2. The component of claim 1, wherein the operative portion of the tool provides a primary function of the tool, which is different than a function of the engaging element which provides temporary engagement between the component and the distal portion of the tool.

3. The component of claim 1, wherein:
the outer portion has an inner surface that defines an interior space in the outer portion of the component that is configured to engage an operative portion of the tool, wherein the operative portion of the tool provides a primary function of the tool; and
the inner portion has an inner surface that defines an interior space in the inner portion of the component that is configured to cooperate with a non-operative portion of the tool, wherein the non-operative portion of the tool provides a function of temporary engagement between the tool and the component, wherein the primary function of the tool is different than the function of temporary engagement.

4. The component of claim 1, wherein:
the outer portion has an inner surface that defines an interior space in the outer portion of the component;
the inner portion has an inner surface that defines a first interior space in the inner portion of the component, and the engaging element is situated in the first interior space, wherein the engaging element includes an inner surface defining a second interior space of the inner portion having a width that is smaller than a width of the first interior space of the inner portion such that:
the width of the first interior space is larger than a width of the interior space of the outer portion; and
the width of the second interior space is smaller than the width of the interior space of the outer portion.

5. The component of claim 1, wherein the engaging element is not fused to the component.

6. The component of claim 1, wherein the engaging element comprises polyetheretherketone.

7. The component of claim 1, wherein the component is a screw, the tool is a screwdriver, and the proximal end of the screw is a screw head.

8. The component of claim 1, wherein the inner potion has a maximum width that is greater than a maximum width of the outer portion.

9. The component of claim 1, wherein the outer portion comprises a hexalobe configuration.

10. The component of claim 9, wherein the inner portion comprises a cylindrical configuration.

11. The component of claim 1, wherein the engaging element includes a lower surface opposite the upper surface, an inner surface and an opposite outer surface, the inner surface of the engaging element defining an opening that is in communication with the inner portion.

12. The component of claim 1, wherein the engaging element includes a lower surface opposite the upper surface, the upper and lower surfaces of the engaging element being free of any projections.

13. The component of claim 1, wherein the engaging element includes a planar lower surface opposite the upper surface, the upper surface being planar such that a distance between the upper and lower surfaces of the engaging element defines a maximum height of the engaging element.

14. The component of claim 1, wherein the engaging element includes a lower surface opposite the upper surface, an inner surface and an opposite outer surface, the engaging element having a gap extending through the lower surface, the upper surface, the inner surface and the outer surface of the engaging element.

15. A fastener with engaging mechanism, the fastener comprising:
a proximal end and a distal end, wherein the proximal end is configured to cooperate with a tool and the proximal end comprises:
- an outer portion having an inner surface that defines an interior space in the outer portion of the fastener that is configured to engage an operative portion of the tool, wherein the operative portion of the tool provides a primary function of the tool;
- an inner portion having an inner surface that defines a first interior space in the inner portion of the fastener that is configured to cooperate with a non-operative portion of the tool; and
- a ledge positioned at an interface between the inner and outer portions; and
an engaging element removably disposed in the inner portion such that an upper surface of the engaging element engages a lower surface of the ledge to retain the engaging element in the inner portion, wherein the engaging element is a C-shaped ring having an inner surface defining a second interior space configured to apply pressure against the non-operative for strengthening a grip that the tool has on the component and provides for a temporary engagement, wherein the non-operative portion of the tool provides a function of temporary engagement between the fastener and a distal portion of the tool, wherein the primary function of the tool is different than the function of temporary engagement.

16. The fastener of claim 15, wherein:
the engaging element is situated in the first interior space the second interior space has a width that is smaller than a width of the first interior space of the inner portion such that:
the width of the first interior space is larger than a width of the interior space of the outer portion; and
the width of the second interior space is smaller than the width of the interior space of the outer portion.

17. The fastener of claim 15, wherein the engaging element is not fused to the fastener.

18. The fastener of claim 15, wherein the engaging element comprises polyetheretherketone.

19. The fastener of claim 15, wherein the fastener is a screw, the tool is a screwdriver, and the proximal end of the screw is a screw head.

20. A system for engaging a fastener and a tool, the system comprising:
a tool with an operative portion and a non-operative portion, wherein the operative portion of the tool provides a primary function of the tool, the non-operative portion of the tool provides a function of temporary engagement between the fastener and a distal portion of the tool, the primary function of the tool is different than the function of temporary engagement, and the non-operative portion of the tool is situated on the tool at a location that is more distal than the operative portion; and a fastener comprising a proximal end and a distal end, wherein the proximal end is configured to cooperate with the tool and the proximal end comprises an inner surface defining:

an outer portion having an inner surface that defines an interior space in the outer portion of the fastener that is configured to engage the operative portion of the tool;

an inner portion; and a ledge positioned at an interface between the inner and outer portions; and an engaging element removably disposed in the inner portion such that an upper surface of the engaging element engages a lower surface of the ledge to retain the engaging element in the inner portion, wherein the engaging element is a C-shaped ring configured to apply pressure against the non-operative for strengthening a grip that the tool has on the component and provides for a temporary engagement.

* * * * *